United States Patent [19]

Garvy, Jr.

[11] Patent Number: 5,153,378
[45] Date of Patent: Oct. 6, 1992

[54] PERSONAL SPACE SHIELDING APPARATUS

[76] Inventor: John W. Garvy, Jr., 465 Crooked Creek Rd., Black Mountain, N.C. 28711

[21] Appl. No.: 698,725

[22] Filed: May 10, 1991

[51] Int. Cl.⁵ ............................................. H05K 9/00
[52] U.S. Cl. ........................... 174/35 R; 174/35 MS; 5/512; 250/515.1
[58] Field of Search .................. 174/35 MS, 35 R; 361/424, 212; 5/414, 508, 512; 250/506.1, 515.1, 517.1

[56] References Cited

U.S. PATENT DOCUMENTS

| | | |
|---|---|---|
| 1,056,712 | 3/1913 | Schweda . |
| 3,867,950 | 2/1975 | Fischell . |
| 3,888,260 | 6/1975 | Fischell . |
| 4,091,818 | 5/1978 | Brownlee et al. . |
| 4,801,807 | 1/1989 | Jacobs . |
| 4,964,408 | 10/1990 | Hink et al. . |
| 5,000,178 | 3/1991 | Griffith . |

FOREIGN PATENT DOCUMENTS 3415961 10/1985 Fed. Rep. of Germany .......... 5/508
1576884 8/1969 France .

OTHER PUBLICATIONS

Sleep Cage, Washington Daily News, city edition, p. 15, Jul. 8, 1953.

Primary Examiner—Leo P. Picard
Assistant Examiner—Bot Lee Ledynh
Attorney, Agent, or Firm—Kennedy & Kennedy

[57] ABSTRACT

An apparatus 10 for shielding a personal occupancy space 11 from electromagnetic and geopathic fields has a floor shield 15 and two side wall shields 18 and 20. The shields are made of ferrous, wire mesh screening and are erected so as to traverse all three spatial protected space. The shields are grounded with the use of a wall plug 29 that has two non-conductive prongs 32 and a conductive grounding prong.

12 Claims, 1 Drawing Sheet

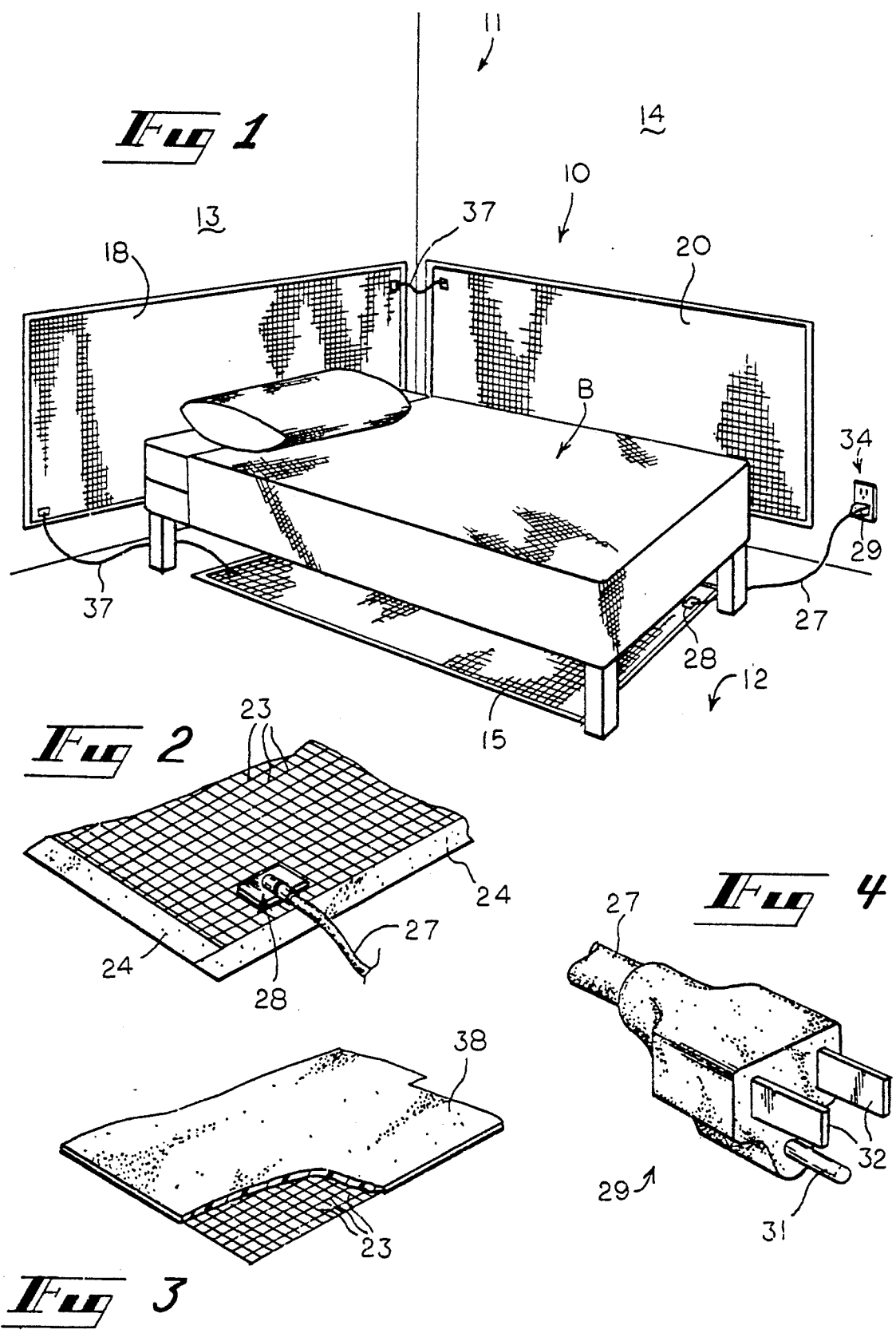

PERSONAL SPACE SHIELDING APPARATUS

TECHNICAL FIELD

This invention relates to apparatus for use in shielding people from electromagnetic and geopathic fields.

BACKGROUND OF THE INVENTION

In the world of today people are exposed not only to natural occurring force fields, such as the earth's magnetic field and geopathic fields, out also from electromagnetic fields created by man. That such fields can produce adverse effects in animals life, and especially in people, has been well documented. Indeed, in May of 1989 the Office of Technology Assessment for the Congress of the United States published *Biological Effects of Power Frequency Electric and Magnetic Fields*. A Pulitzer prize was recently won by Paul Brodeur for his book, *The Zapping of America*.

The existence of resultant ill effects in animal life can be detected with the use of bioelectric function diagnostic technology such as with Vegatest equipment. This is described in detail in *Modern Techniques of Acupuncture*. Volume III by Dr. Julian Kenyon and in numerous articles published by the internationally known German practitioner and teacher, Helmut Schimmel, M.D.

Heretofore, little has been done to protect people, and other forms of animal life, from the adverse effects of electromagnetic and geopathic energy except in the immediate vicinity of high power generating power distribution substations and high power transmission lines. The universal attitude has essentially been "out of sight, out of mind" except in such acute situations like that which occurred in the United States Embassy in Moscow, U.S.S.R. several years ago when it was heavily irradiated with microwave energy. Though shielding of equipment, cables and electronic components has long been practiced, little has been done to protect people. In the acute American Embassy situation, which is believed to have produced leukemia and pre-leukemic blood conditions in staff personnel, a sheet of aluminum foil was simply erected on a wall that faced the source of microwave energy. But in ordinary daily life situations, such as those involving sleep and work, little has been done to shield people from energy force fields.

SUMMARY OF THE INVENTION

It has now been discovered that the placement of grounded ferrous screens about a personal occupancy space so that the screen traverse all three spatial dimensions adjacent to the space, serves to protect people occupying the space from the adverse effects of electromagnetic and geopathic field forces. For example, by placing wire mesh galvanized steel screens beneath sleeping beds and along two contiguous sides of the beds, people suffering insomnia have been able to sleep better and to improve symptomatically. Though erecting such screens around all sides of the space so as to enclose it completely, works at least as well, surprisingly, such has been found not usually to be necessary.

BRIEF DESCRIPTION OF THE DRAWING

FIG. 1 is a perspective view of apparatus embodying principles of the present invention in a preferred form shown erected above a bed.

FIG. 2 is an enlarged perspective view of a corner portion of the screen shown in FIG. 1.

FIG. 3 is an enlarged perspective view of a corner portion of the screen in an configuration.

FIG. 4 is an enlarged perspective view of the plug shown of the apparatus in FIG. 1.

DETAILED DESCRIPTION

With reference next to the drawings, there is shown an apparatus 10 for shielding a bed B located in a corner of a room in a space 11. The space is partially bounded by a room floor 12, a side wall 13 and a contiguous side wall 14 that extends normally from side wall 13. The apparatus has an electrically conductive floor shield 15 sized to cover the area of the floor directly beneath the bed B. It also has an electrically conductive side shield 18 mounted uprightly on the side wall 13 which is sized to shield the width of the bed and at least a height of the space occupied by a person reclined upon the bed. Similarly, it further has an electrically conductive side shield 20 mounted uprightly to side wall 14 which is sized to shield the length of the bed and at least the height of the space occupied by a reclined person.

The apparatus 10 also has an electrical conductor 27 releasibly connected to a coupler 28 mounted to the floor shield 23. Conductor 27 terminates in an electrical plug 29 of special construction. Plug 29 has an electrically conductive grounding prong 31 connected to the conductor 27, and two electrically non-conductive prongs 32 which may, for example, be plastic. The plug may be inserted into a conventional, three prong receiving wall socket 34 with the grounded prong 31 coupled with the wall socket ground and with the prongs 32 only providing mechanical support and structural integrity. The apparatus also has electrical conductors 37 with couplers 38 on each of their ends which are mounted to shields so as to connect all of them together electrically.

The wire mesh screening of the shields are preferably made of galvanized steel which may be alloyed with cooper or aluminum. It has been found that the width of the wire grid interstices should be no more than 2.5 centimeters across. The border of the screening is preferably framed within strips of vinyl to prevent the grid from separating and also to provide personal protection from exposed wire ends. Alternatively, as shown in FIG. 3, the screening may be embedded or overlaid on one side with a flexible layer 38 of plastic for aesthetics.

Although the shields are preferably flat, flexible and distinct, this is not essential. For example, two or even all three may be hinged together in which case the conductors 37 are not required. Indeed, a single unitary screen could be used provided that it traverses all three spatial dimensions adjacent the space.

From the foregoing, it is seen that apparatus is now provided for shielding personal occupancy spaces and any persons therein from adverse biological effects of electromagnetic and geopathic energy force fields. It should however be understood that the just described embodiment merely illustrates principles of the invention in a preferred from. Many modifications, additions and deletions may be made thereto without departure from the spirit and scope of the invention as set forth in the following claims.

I claim:

1. Apparatus for shielding a personal occupancy space such as a sleeping space or working space from ambient electromagnetic and magnetic energy which comprises ferrous screening sized to cover the bottom and two adjacent sides of the space, and grounding means for grounding said ferrous screening, said grounding means includes a wall plug having a plurality of plugs with one plug being electrically conductive and the other plug being electrically non-conductive.

2. The apparatus of claim 1 wherein said screening is comprised of wire mesh screening material.

3. The apparatus of claim 2 wherein said wire mesh screening material has interstices of sizes less than 2.5 centimeters across.

4. The apparatus of claim 1 wherein said screening material comprises galvanized steel.

5. Apparatus for shielding a personal occupancy space from ambient electromagnetic and magnetic fields comprising, in combination, an electrically conductive floor shield sized to underlie a substantial portion of the occupancy space supported along a bottom boundary of the occupancy space, a first electrically conductive side shield mounted uprightly to one side of the occupancy space sized to cover a substantial portion of a side boundary of the occupancy space, a second electrically conductive side shield mounted uprightly to another side of the occupancy space adjacent to the one side sized to cover a substantial portion of another side boundary of the occupancy space, each of said shields being spaced apart from each other, and electrical grounding means grounding said floor shield and grounding said first and second side shields.

6. The apparatus of claim 5 wherein said shields are comprised of wire mesh screening.

7. The apparatus of claim 6 wherein said wire mesh screening has interstices of sizes less than 2.5 centimeters across.

8. The apparatus of claim 5 wherein said shields are comprised of galvanized steel.

9. The apparatus of claim 8 wherein said shields are further comprised of a metal selected from the group consisting of copper and aluminum.

10. The apparatus of claim 5 wherein said grounding means comprises conductors electrically connecting together said floor shield and said first and second side shields.

11. The apparatus of claim 5 wherein each of said shields is substantially flat.

12. Apparatus for shielding a personal occupancy space from ambient electromagnetic and magnetic fields comprising, in combination, an electrically conductive floor shield sized to underlie a substantial portion of the occupancy space supported along a bottom boundary of the occupancy space, a first electrically conductive side shield mounted uprightly to one side of the occupancy space sized to cover a substantial portion of a side boundary of the occupancy space, a second electrically conductive side shield mounted uprightly to another side of the occupancy space adjacent to the one side sized to cover a substantial portion of another side boundary of the occupancy space, and electrical grounding means grounding said floor shield and grounding said first and second side shields, said grounding means comprises a three prong plug with one of said prongs being electrically conductive and two others of said prongs being electrically non-conductive.

* * * * *